US009188563B2

(12) United States Patent
Mohammadi et al.

(10) Patent No.: US 9,188,563 B2
(45) Date of Patent: Nov. 17, 2015

(54) PERFORATED MOS STRUCTURE FOR SINGLE BIOMOLECULE DETECTION

(71) Applicant: Purdue Research Foundation, West Lafayette, IN (US)

(72) Inventors: Saeed Mohammadi, Zionsville, IN (US); Mojgan Sarmadi, Zionsville, IN (US); Hossein Pajouhi, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 0 days.

(21) Appl. No.: 14/497,864

(22) Filed: Sep. 26, 2014

(65) Prior Publication Data

US 2015/0083597 A1 Mar. 26, 2015

Related U.S. Application Data

(60) Provisional application No. 61/882,657, filed on Sep. 26, 2013.

(51) Int. Cl.
*G01N 27/414* (2006.01)
*G01N 33/487* (2006.01)

(52) U.S. Cl.
CPC ...... *G01N 27/4145* (2013.01); *G01N 33/48721* (2013.01)

(58) Field of Classification Search
CPC .............. G01N 27/4145; G01N 33/48721
See application file for complete search history.

(56) References Cited

U.S. PATENT DOCUMENTS

| 4,411,741 | A | * | 10/1983 | Janata ........................... 257/253 |
| 4,486,292 | A | * | 12/1984 | Blackburn ..................... 204/416 |
| 4,881,109 | A | * | 11/1989 | Ogawa .......................... 257/253 |
| 4,947,104 | A | * | 8/1990 | Pyke ............................. 324/71.5 |
| 5,140,393 | A | * | 8/1992 | Hijikihigawa et al. ....... 257/252 |
| 5,591,321 | A | * | 1/1997 | Pyke ............................. 205/787 |
| 6,914,279 | B2 | * | 7/2005 | Lu et al. ......................... 506/39 |
| 7,151,301 | B2 | * | 12/2006 | Yoo et al. ...................... 257/401 |
| 7,329,387 | B2 | * | 2/2008 | Fukutani et al. .......... 422/82.01 |
| 8,066,945 | B2 | * | 11/2011 | Willett et al. ............. 422/82.01 |
| 2010/0006451 | A1 | * | 1/2010 | Gordon et al. ............. 205/777.5 |
| 2012/0134880 | A1 | * | 5/2012 | Kurkina et al. ............ 422/82.01 |

OTHER PUBLICATIONS

Zhao Lu, et al., A Hybrid bacteria and microparticle detection platform on a CMOS chip: Design, simulation and testing considerations, 2008.

(Continued)

*Primary Examiner* — Lex Malsawma
(74) *Attorney, Agent, or Firm* — Purdue Research Foundation

(57) ABSTRACT

A perforated metal oxide semiconductor (MOS) structure for single biomolecule, virus, or single cell detection is disclosed. The structure includes a nanochannel formed through a sensing region configured to allow a solution containing particles to pass through the perforated MOS sensor. First and second terminals are configured to measure electrical parameters representative of change of electrical characteristics of the solution as the particle passes through the perforated MOS structure.

10 Claims, 4 Drawing Sheets

(56) References Cited

OTHER PUBLICATIONS

Hui Tang, et al., An Impedance Microsensor With Coplanar Electrodes and Vertical Sensing Apertures, IEEE Sensors Journal, 2005, vol. 5, No. 6, 1346-1352.

Giseok Kang, et al., Differentiation Between Normal and Cancerous Cells at the Single Cell Level Using 3-D Electrode Electrical Impedance Spectroscopy, IEEE Sensors Journal, 2012, vol. 12, No. 5, 1084-1089.

* cited by examiner

PERFORATED MOS STRUCTURE FOR SINGLE BIOMOLECULE DETECTION

RELATED APPLICATIONS

The present application claims the benefit of U.S. provisional application Ser. No. 61/882,657, filed Sep. 26, 2013, the contents of which are hereby incorporated by reference in its entirety.

TECHNICAL FIELD

The present disclosure generally relates to detection and measurement arrangements and in particular to an arrangement for detecting single biomolecules, viruses, or single cells.

BACKGROUND

Over the past few decades, the ability to measure, separate, and discriminate microscopic particles has improved. Tools are now available to probe individual cells. These tools are often complicated, expensive, and require sophisticated measurements techniques. For example, testing a water sample for certain waterborne particles (e.g., bacteria) can require equipment with significant sophistication. Furthermore, where presence of particles is to be detected and nature of particles measured based on a statistical approach (i.e., hundreds and thousands of samples are to be tested), such an approach adds further sophistication to testing equipment.

Single-biomolecule detection has been proposed using a variety of techniques such as mass spectroscopy, surface-enhanced Raman spectroscopy, patch clamp, single-molecule fluorescence microscopy with enhanced imaging using photomultiplier tubes or avalanche photodiodes, atomic force microscopy, and nano-manipulator and nano-resonator technologies [50-51]. In many of these techniques, the observation of one molecule requires its prior isolation. Other considerations including sample preparation, sensitivity, and specificity in each of these techniques limit their applications to specific categories of biomolecules.

In various applications where it is desired to obtain information about nucleotides (T, A, C, or G) of a DNA or RNA strand, such information is not readily available with modern detection arrangements.

Therefore, there is an unmet need for a tester arrangement capable of detecting and measuring particles of various sizes that can be scaled up to provide statistical results based on detecting large numbers of samples.

BRIEF DESCRIPTION OF THE DRAWINGS

The above and other objects, features, and advantages of the present invention will become more apparent when taken in conjunction with the following description and drawings wherein identical reference numerals have been used, where possible, to designate identical features that are common to the figures, and wherein.

Figure 1:
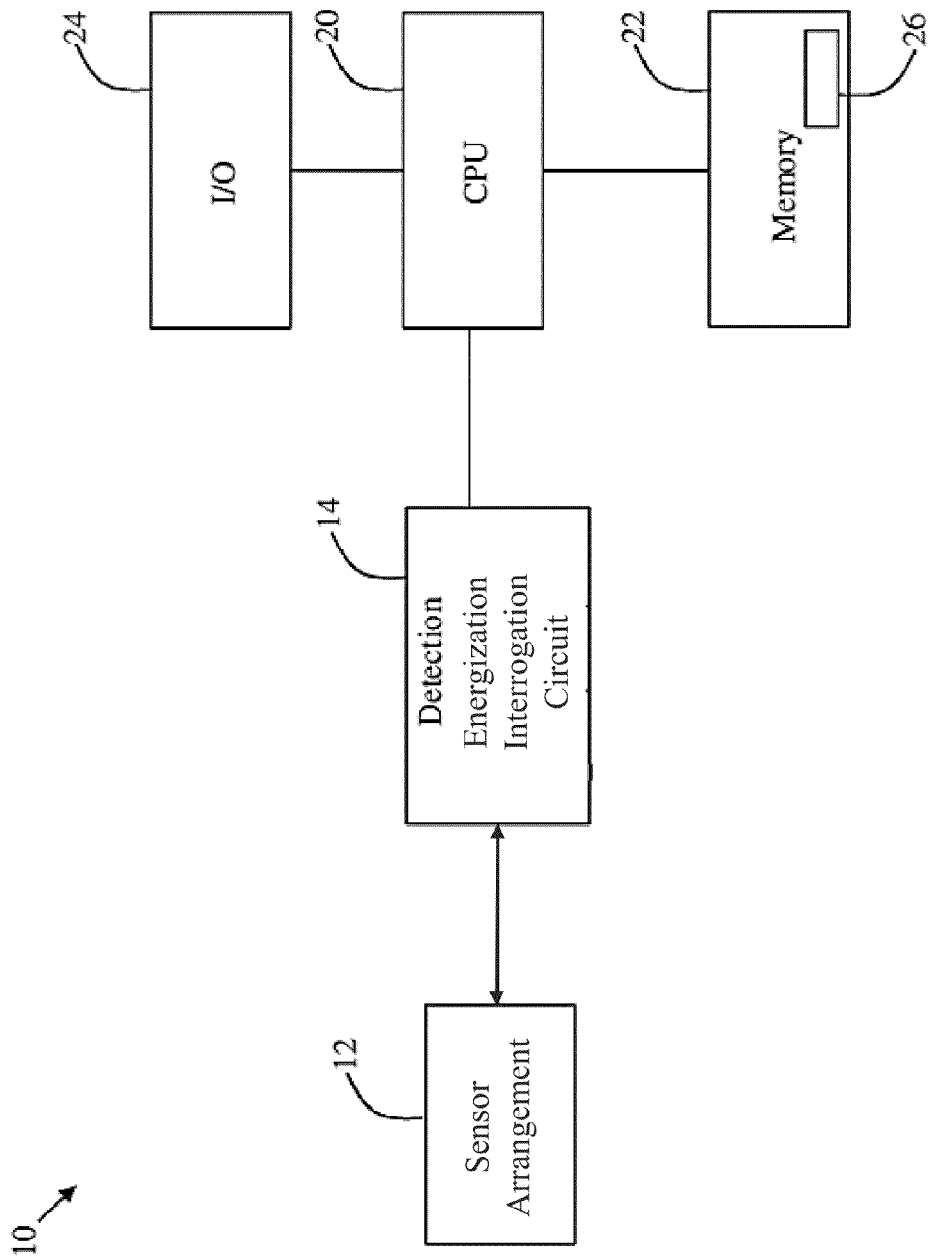
FIG. 1 shows a block diagram of a system according to one embodiment.

The attached drawings are for purposes of illustration and are not necessarily to scale.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

A novel detection and measurement arrangement is described that is capable of detecting and measuring particles of various sizes that can be scaled up to provide statistical results based on detecting large numbers of samples. The novel arrangement includes semiconductor process-based nanosensors that are configured to selectively separate and measure particles. In particular, the nanosensors are configured to selectively allow particles of various sizes through nanochannels formed in the nanosensors and measure electrical characteristics of those particles while passing through. The types of particles include, but are not limited to, biomolecules such as DNA, viruses, cells or other material. Complementary metal oxide semiconductor (CMOS) devices built on silicon on insulator (SOI) integrated circuits are used to implement CMOS amplifiers along with the footprints of perforated metal oxide semiconductor (MOS) sensors. Thereafter, perforated MOS sensors and fluidic nanochannels are post-processed on the CMOS integrated circuits to achieve biosensors capable of detecting single biomolecules.

FIG. 1 is a block diagram of an exemplary system for energization and interrogation of a particle detection and measurement arrangement, according to the present disclosure. The system 10 includes a sensor arrangement 12, an energization-interrogation circuit block 14, a processing circuit 20, a memory block 22 and an input/output (I/O) device 24. The I/O device 24 may include a user interface, a graphical user interface, keyboards, pointing devices, remote and/or local communication links, displays, and other devices that allow externally generated information to be provided to the system 10, and that allow internal information of the system 10 to be communicated externally.

The processing circuit 20 may suitably be a general purpose computer processing circuit such as a microprocessor and its associated circuitry. The memory block 22 may suitably be various memory and data storage elements associated with a general purpose computer. Within the memory block 22 are various instructions in a program instruction block 26 within the memory block 22. The processing circuit 20 is configured to execute the program instructions 26 to carry out the various operations.

The processing circuit 20 is also connected to the I/O device 24 to receive data from, and present data to a user. The processing circuit 20 is also connected to the energization-interrogation circuit block 14 to receive data from, and send data to, the energization-interrogation circuit block 14. The data communicated between the processing circuit 20 and the energization-interrogation circuit block 14 includes the energization signal as well as the readout data (also referred to herein as the interrogation data).

The memory block 22 may include random access memory (RAM), read only memory (ROM), programmable read only memory (PROM), erasable programmable read only memory (EPROM), or electrically erasable read only memory (EEPROM), and other types of memory known in the art suitable for storing data. The data may be of the type that continuously changes, or of the type that changes during operations of the energization-interrogation circuit block 14.

Figure 2:
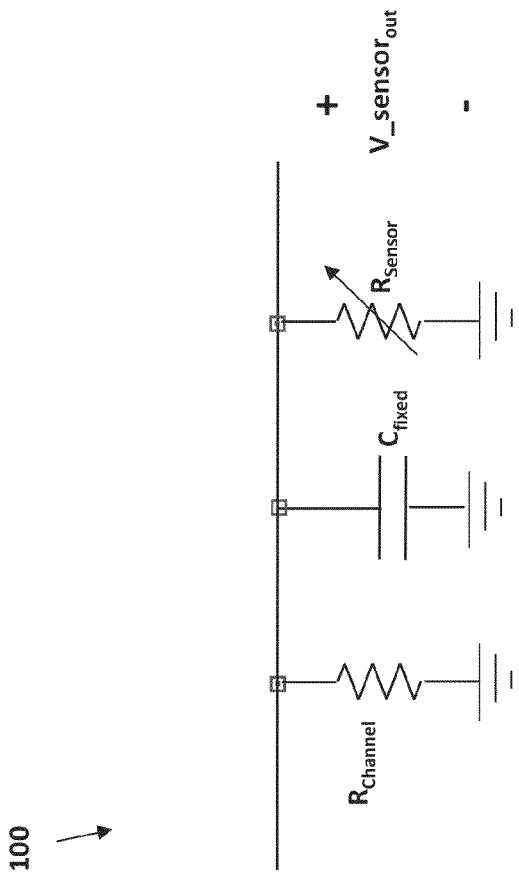
FIG. 2 is an electrical schematic representing a lumped parameter model of a sensor arrangement of FIG. 1 according to one embodiment.

Referring to FIG. 2, an electrical schematic is depicted representing a lumped parameter model 100 of the sensor arrangement 12 in a parallel connectivity manner. The model 100 includes a fixed resistance, identified as $R_{Channel}$, a fixed capacitance identified as $C_{fixed}$, and a variable resistance identified as $R_{sensor}$. A voltage across the parallel connection, i.e., the voltage out of the model 100, is identified as V_sensor$_{out}$. The lumped parameter model 100 is based on a model for a MOS transistor (not shown) having two terminals, referred to herein as sensing terminals, for measuring various electrical characteristics. As will become more clear below with reference to FIG. 4, the gate and source regions of the MOS sensor constitute the electrical sensing portion allowing measurements of various parameters, e.g., resistance and capacitance of across a fluidic channel when a solution that contains particles passes through the fluidic channel, also referred to herein as the nanochannel disposed within the nanosensor. In that sense, the $R_{channel}$ and the $C_{fixed}$ represent the resistance and capacitance across the fluidic channel, respectively.

Figure 3:
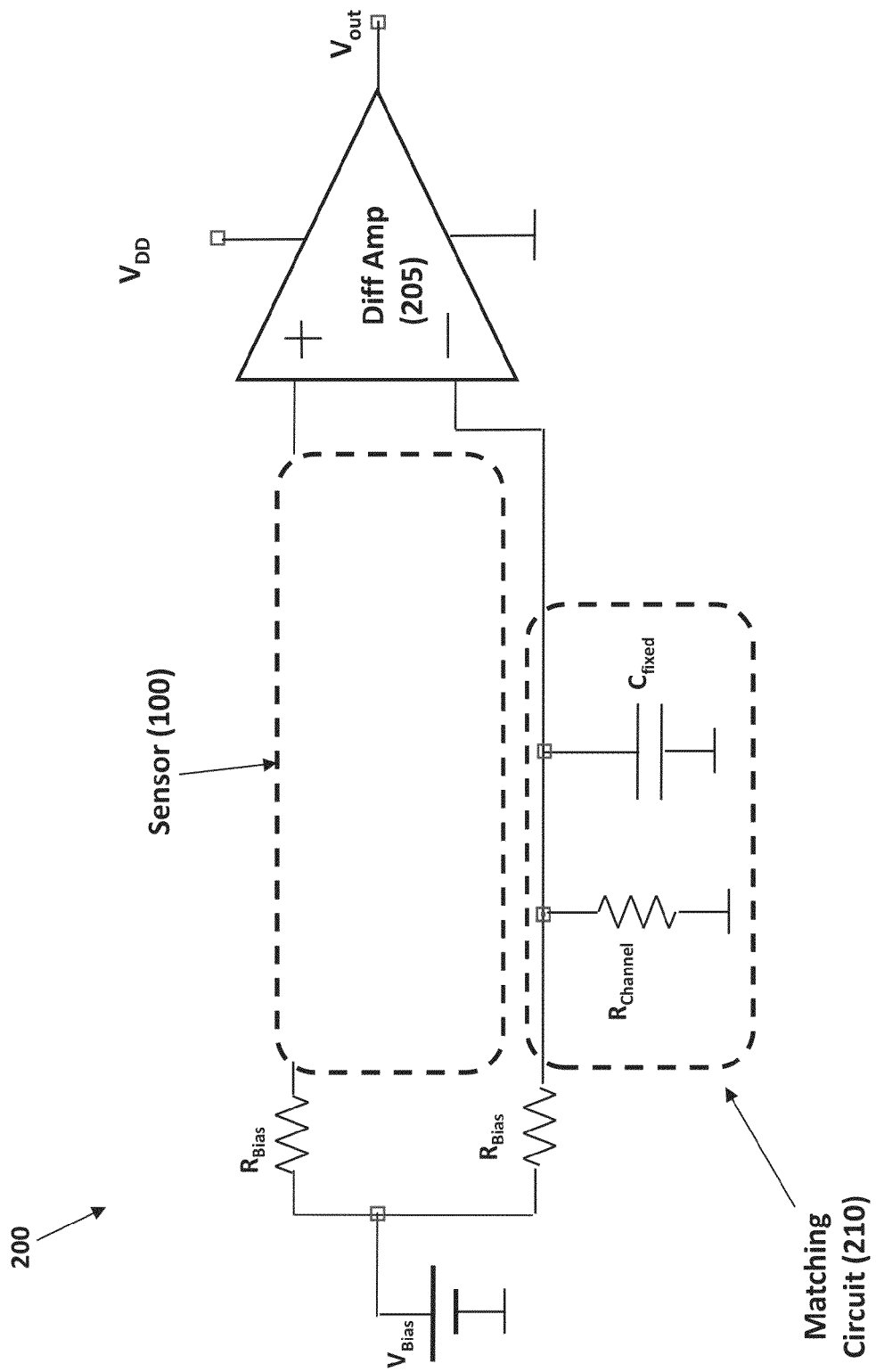
FIG. 3 is an electrical schematic representing a lumped parameter model which includes the model of FIG. 2 and other components of the system of FIG. 1 according to one embodiment.

Referring to FIG. 3, a schematic is depicted representing a lumped parameter model 200 including both the model 100 for the sensor arrangement as well as components representing the energization/interrogation circuit 14 (as shown in FIG. 1). The model 200 includes a voltage source identified as $V_{Bias}$, and a voltage source identified as $V_{DD}$. The $V_{DD}$ powers a differential amplifier 205. The $V_{Bias}$ source is coupled to a pair of $R_{Bias}$ resistors, one coupled to the sensor model 100 and one coupled to a matching circuit 210. The matching circuit 210 includes components which are configured to match the fixed components of the sensor model 100. These components include $R_{Channel}$ and $C_{fixed}$, which as described above represent resistance and capacitance across the fluidic channel as a solution containing particles passes through the fluidic channel. These components are coupled to each other in a parallel manner. Outputs of the sensor model 100 and the matching circuit 210 are coupled to inputs of the differential amplifier 205. The output of the differential amplifier 205 is identified as $V_{out}$, which is coupled to the processing circuit 20 (as depicted in FIG. 1). The $V_{Bias}$ is a bias voltage that can be applied across the perforated MOS sensor to invert its electrical channel and allow the detection.

The differential amplifier is configured to amplify changes brought on by changes represented by $R_{sensor}$. The matching circuit removes effects of the fixed components represented by $R_{Channel}$ and $C_{fixed}$ by matching those components and the $R_{Bias}$ resistors which are all powered by the same source $V_{Bias}$, via common mode rejection characteristics of the operational amplifier. When the source is applied as an alternating current signal, the imaginary portion of the measured signal may be used to determine the polarity of the biomolecule. Such polarity measurement may be useful in determining various parameters of the biomolecule.

Figure 4:
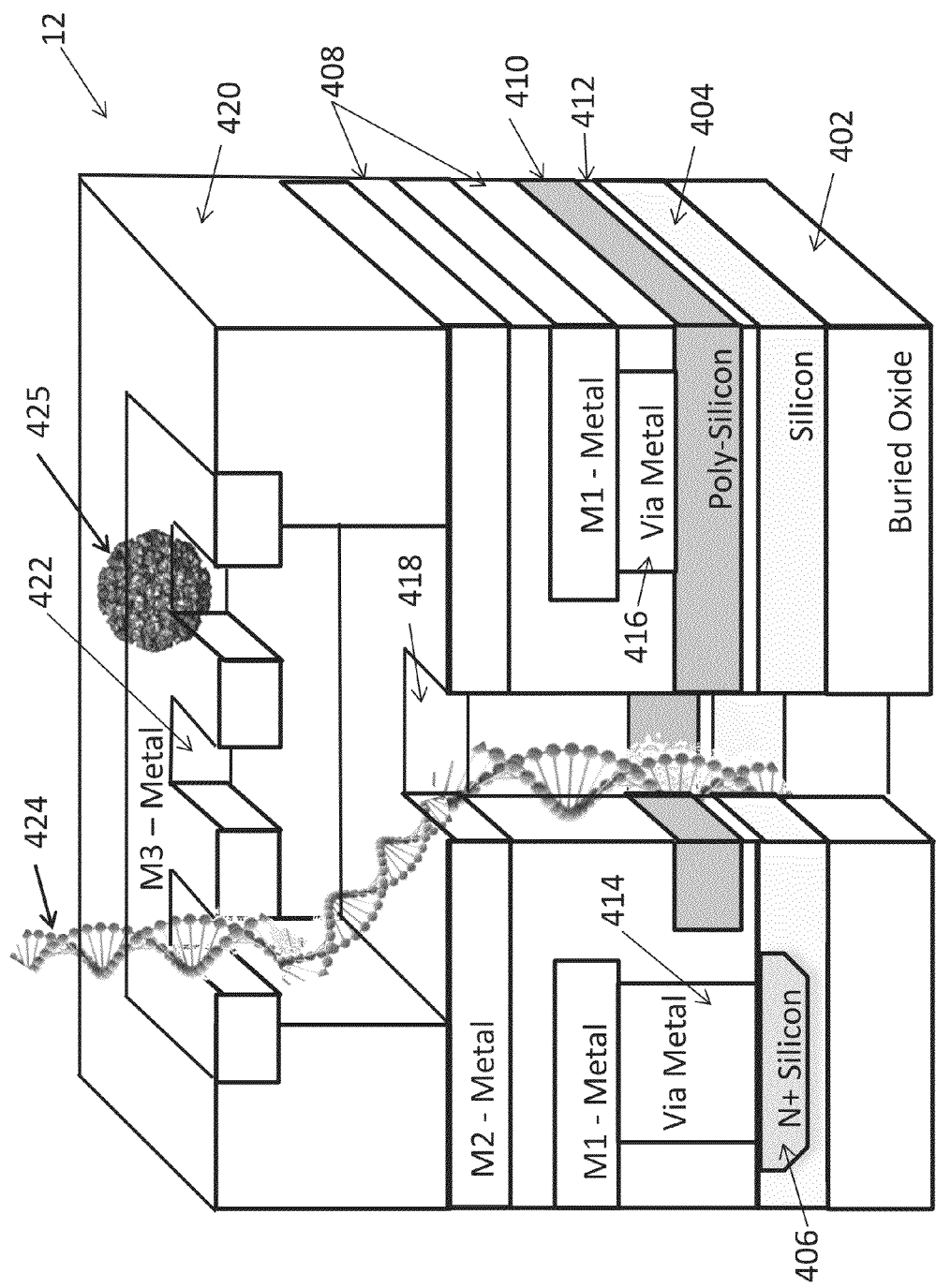
FIG. 4 is a perspective view schematic of the sensor arrangement of FIG. 1 according to one embodiment.

Referring to FIG. 4, a perspective view schematic of the sensor arrangement 12 is depicted. In the illustrated embodiment, the sensor arrangement 12 includes a buried oxide layer 402 and a doped silicon substrate 404 disposed thereon including a region of highly doped N+ material 406. Disposed over the silicon substrate 404 is a layer of silicon oxide 408. Within the silicon oxide layer 408 are layers of poly-silicon 410 and various metal layers, e.g., metal layers one (M1), two (M2), and three (M3). The poly-silicon layer 410 is disposed immediately above the silicon substrate 404 within the oxide layer 408. A portion 412 of the oxide, directly below the poly-silicon layer 410 is referred to as the gate oxide. One of the two sensing terminals (i.e., gate terminal, not shown but coupled to the metal one layer M1 positioned above the polysilicon layer 410) is coupled to the poly-silicon layer 410. The metal one layer M1 is coupled to the N+ doped silicon region 406 with metal vias 414. The second sensing terminal (i.e., source terminal, not shown but coupled to the metal one layer M1 positioned above the N+ doped silicon region 406) is coupled to the N+ doped silicon region 406. The metal one layer M1 is also coupled to the poly-silicon layer 410 with metal vias 416. An elongated though-hole structure 418, e.g., cylindrical or cuboid in shape, is formed through the metal two layer M2, silicon oxide 408, poly-silicon 410, silicon substrate 404, and buried oxide layer 402. The through-hole 418 (also referred to as the nanochannel and fluidic channel) is sized to allow desired particles through. Formed on top of the metal two layer M2 are an additional silicon oxide layer 420 and a metal three layer M3. The metal three layer M3 is formed in the shape of a mesh having openings 422 configured to prevent particles of one size (e.g., particle 425) or higher through.

Various approaches can be implemented to cause movement of particles in the fluid, that are to be detected and measured, through the nanochannel 418. In one embodiment, electrodes (not shown) can be coupled to metal three layer M3 and the silicon substrate 404 in order to provide a voltage gradient to the particles, such as particle 424 to encourage the particle to travel through the nanochannel 418. Such a voltage gradient can be applied by coupling the desired voltage to a terminal (not shown) coupled to metal three layer M3 mesh and a terminal (not shown) to the substrate 404. In another embodiment, a pressure gradient can be applied across the nanochannel 418 to similarly encourage fluid to travel through the nanochannel 418. The pressure gradient can be applied utilizing a pump (not shown) or a vacuum (not shown) placed near the metal three layer M3 or the silicon substrate 404, respectively.

The differential amplifier 205, depicted in FIG. 3, is connected to the sensor arrangement 12 by coupling to metal one layer M1. The coupling (not shown) can be a direct metal interconnection or may include a bump, wire-bond, and other coupling arrangements known to a person having ordinary skill in the art. Alternatively, the MOS sensor 12 can be fabricated using the same integrated circuit manufacturing process as the amplifier 205 such that the two components are integrated onto the same device, chip or integrated circuit. As such, signal corrupting factors normally present when an amplifier is located remotely from a sensor using extended leads, such as electrical noise, signal attenuation and other external factors, can be minimized.

In one embodiment, a large number of parallel nanochannels 418 with approximate minimum dimensions of about 50 nm by about 50 nm by about 2 μm can be generated. Each nanochannel 418 is embedded within a perforated MOS sensor 12 that is formed by forming a vertical nanochannel 418 through the center of a horizontal MOS structure as shown in FIG. 4. Each perforated MOS structure 12 is a partially floating body CMOS SOI transistor with at least two contacts: a polysilicon sensing terminal (electrically connected to layer 410) and a N+ sensing terminal (electrically connected to layer 404). The layers 410 and 404 are separated by the thin gate oxide layer 412. These terminals can be used to measure a floating ionic current in the nanochannel 418, given the free ions in the solution. The ionic current is measured across the perforated MOS sensor 12 with the constant resistance $R_{Channel}$. If a particle, such as biomolecule 424, or a small segment of a particle goes across the two terminals of the perforated MOS sensor 12, the detected ionic current is modified. The net effect measured by the perforated MOS sensor 12 is the variable sensor resistance $R_{sensor}$ as shown in FIG. 2. The current variation (depending on the charge of the polarity of the atoms of the DNA biomolecule 424 next to each electrode by the nucleotides of the DNA biomolecule 424 as it translocates through the nanochannel 418) and the duration of the change can be correlated to the length of type of particles, e.g., DNA molecules, that pass through the nanochannels 418. Also, because the gate oxide layer 412 can be made extremely thin, the probability that a biomolecule 424 will make successful contact with both terminals is greatly increased.

DNA entropy and nanochannel-DNA interaction can affect the velocity of the DNA molecules during translocation through the fluidic nanochannel 418. Furthermore, since the information that is collected from the DNA molecules is based on the period the molecules require to pass through the fluidic nanochannel 418, unwanted velocity variations can play havoc with measurements. However, the arrangement depicted in FIG. 4 including the provisions for controlling the velocity of the solution, which include DNA molecules 418, i.e., based on applying a voltage or pressure gradient, advantageously control the velocity of the DNA molecule 418 as it translocates through the nanochannel 418. Therefore, the molecule velocity is set to predictable levels in accordance with the parameters of the nanochannel and the voltage/pressure gradient.

The MOS sensor 12 can be fabricated by utilizing multiple etching processes. While not shown in FIG. 4, a top layer is used as a masking layer for post-processing. The top layer (not shown) which may be an aluminum (Al) contact layer or a passivation layer (Polyimide, $Si_3N_4$ or similar material) or a combination of both layers is disposed above metal three layer M3 and an oxide layer above the metal three layer M3. In order to fabricate the fluidic channel 418, three etching procedures are carried out, in one exemplary embodiment. First, the oxide layer directly underneath the masking layer is etched away using an exemplary etching process, e.g., reactive ion etching. The etching continues until a cavity is formed between the opening in the masking layer (top metal or passivation layer, not shown) and metal two layer M2. In the etching process, the meshing layer (metal three layer M3) and a portion of the fluid channel 418 are formed. Next, another etching process is performed, this time from the bottom of the MOS sensor 12 all the way to the partially formed fluidic channel 418 using an exemplary etching process, e.g., $XF_2$ etching of the buried oxide 402 and the doped silicon 404. This etching step is carried out and continues until a second cavity inside the Si substrate underneath the desired fluid channel 418 is formed. The final etching step uses another exemplary etching process, e.g., a reactive ion etching process to etch the material between the top and bottom cavities formed by the last two etching steps. This etching step starts from the top of the MOS sensor 12 and uses Metal 2 layer M2 as a masking layer to etch oxide and form the nano fluidic channel 418.

The fabrication steps discussed above are intended as exemplary steps and no limitation should be read into these steps. Other process steps, known to a person having ordinary skill in the art, can be implemented to form the fluidic channel 418. Furthermore, it will be appreciated that the fabrication steps discussed above can be used on multiple (thousands) MOS sensors disposed on a wafer (known as batch fabrication). It shall be further understood that the nanochannel 418 may be formed to accommodate various sizes and type of biomolecules including, but not limited to, DNA, viruses, cells and the like.

In operation, by applying a voltage/pressure gradient across the fluidic nanochannel 418 of the MOS sensor 12, i.e., between the terminal (not shown) coupled to the mesh of metal three layer M3 and the terminal (not shown) coupled to the substrate 404 or a pressure gradient across the MOS sensor 12, DNA molecules 424 and/or other particles are encouraged to pass through the nanochannel 418 at a specific translocation velocity. The translocation velocity can be made proportional to a parameter associated with the gradient, e.g., voltage or pressure. As the solution passes through the nanochannel 418 a pass-through current and capacitance can be measured across the perforated MOS sensor 12, by measuring various parameters across the sensing terminals. The solution particles of a specific size can pass through metal three layer M3 mesh while larger size particles are stopped from flowing through. As a DNA molecule 424 passes through the fluidic nanochannel 418 at a predetermined velocity, a change in the pass-through current and capacitance occurs that can be measured across the sensing terminals. The nature of the change and the duration of the change can be correlated to different constituents of the DNA molecule 424.

Furthermore, by applying a voltage to metal two layer M2, the particles in the solution can be further encouraged to approach the perforated MOS sensor 12 and begin translocation through the sensor.

It should be appreciated that while only one MOS sensor 12 is shown, a plurality of these sensors can be utilized in a measurement system in order to obtain statistical data associated with the particles in a solution. The MOS sensors 12 can be implemented in large numbers, e.g., hundreds or thousands, to provide accurate statistical data.

Those skilled in the art will recognize that numerous modifications can be made to the specific implementations described above. The implementations should not be limited to the particular limitations described. Other implementations may be possible.

The invention claimed is:

1. A perforated metal oxide semiconductor (MOS) sensor, comprising:
   a sensing portion including
      a doped substrate;
      a highly doped region disposed within the substrate;
      an oxide layer disposed on the substrate;
      a first metal portion coupled to the highly doped region;
      a first terminal coupled to the first metal portion;
      a poly-silicon layer disposed within the oxide layer;
      a second metal portion coupled to the poly-silicon layer;
      a second terminal coupled to the second metal portion;
   a nanochannel formed through the sensing portion configured to allow a solution containing particles to pass through the perforated MOS sensor, the doped substrate, and the poly-silicon layer, wherein the first terminal and the second terminal are configured to measure electrical parameters representative of change of electrical characteristics of the solution as a particle passes through the perforated MOS sensor.

2. The perforated MOS sensor of claim 1, further comprising:
   a mesh disposed above the sensing portion, the mesh configured to prevent particles of a predetermined size or larger from passing through the mesh.

3. The perforated MOS sensor of claim 2, the mesh constructed utilizing a third metal portion.

4. The perforated MOS sensor of claim 3, further comprising:
   a third terminal coupled to the third metal portion of the mesh; and
   a fourth terminal coupled to the substrate.

5. The perforated MOS sensor of claim 1, the first and second metal portions are constructed utilizing a metal layer in a MOS manufacturing process.

6. The perforated MOS sensor of claim 3, the third metal portion is constructed utilizing a metal layer in the MOS manufacturing process.

7. The perforated MOS sensor of claim 4, the third and fourth terminals further configured to provide a voltage gradient across the MOS sensor to cause particles within the solution to travel through the nanochannel at a predetermined velocity.

8. The perforated MOS sensor of claim 1, further configured to apply a pressure gradient across the MOS sensor to bias particles within the solution to travel through the nanochannel at a predetermined velocity.

9. The perforated MOS sensor of claim 1, further comprising an amplifier circuit, wherein the amplifier circuit and the MOS sensor are integrated within a single chip.

10. The perforated MOS sensor of claim 1, wherein the particle is a biomolecule, a virus, or a single cell.

\* \* \* \* \*